(12) United States Patent
Llabjani

(10) Patent No.: US 12,084,642 B2
(45) Date of Patent: Sep. 10, 2024

(54) CELL CULTURE DEVICE

(71) Applicant: ReVivoCell Limited, Lancaster (GB)

(72) Inventor: Valon Llabjani, Lancaster (GB)

(73) Assignee: REVIVOCELL LIMITED, Lancaster (GB)

( * ) Notice: Subject to any disclaimer, the term of this patent is extended or adjusted under 35 U.S.C. 154(b) by 370 days.

(21) Appl. No.: 16/075,136

(22) PCT Filed: Feb. 6, 2017

(86) PCT No.: PCT/GB2017/050286
§ 371 (c)(1),
(2) Date: Aug. 2, 2018

(87) PCT Pub. No.: WO2017/134464
PCT Pub. Date: Aug. 10, 2017

(65) Prior Publication Data
US 2018/0371390 A1 Dec. 27, 2018

(30) Foreign Application Priority Data
Feb. 5, 2016 (GB) ...................... 1602146

(51) Int. Cl.
C12M 1/12 (2006.01)
C12M 1/00 (2006.01)
(Continued)

(52) U.S. Cl.
CPC ............ *C12M 23/04* (2013.01); *C12M 23/12* (2013.01); *C12M 23/34* (2013.01); *C12M 25/02* (2013.01);
(Continued)

(58) Field of Classification Search
CPC ...... C12M 23/04; C12M 23/12; C12M 23/34; C12M 23/38; C12M 25/02; C12M 25/14; C12M 3/06
See application file for complete search history.

(56) References Cited

U.S. PATENT DOCUMENTS

| 5,958,762 A | 9/1999 | Stoppini et al. |
| 6,991,652 B2 * | 1/2006 | Burg ................ A61L 27/48 424/424 |

(Continued)

FOREIGN PATENT DOCUMENTS

| WO | 1993/011498 A1 | 6/1993 |
| WO | 2007/021919 A1 | 2/2007 |

(Continued)

OTHER PUBLICATIONS

International Search Report and Written Opinion for International Application No. PCT/GB2017/050286 (mailed May 19, 2017).
(Continued)

*Primary Examiner* — Lydia Edwards
(74) *Attorney, Agent, or Firm* — Troutman Pepper Hamilton Sanders LLP (Rochester)

(57) ABSTRACT

A cell culture device comprising a container, at least one divider and a plurality of cell growth blocks located within the container. The divider separates the container into multiple compartments and is selectively permeable. The cell growth blocks are each independently removable from the container. Also disclosed is a cell growth block comprising a three dimensional scaffold located within a selectively permeable housing, a kit for a cell culture device and a method of culturing cells.

55 Claims, 3 Drawing Sheets

Figure 1:
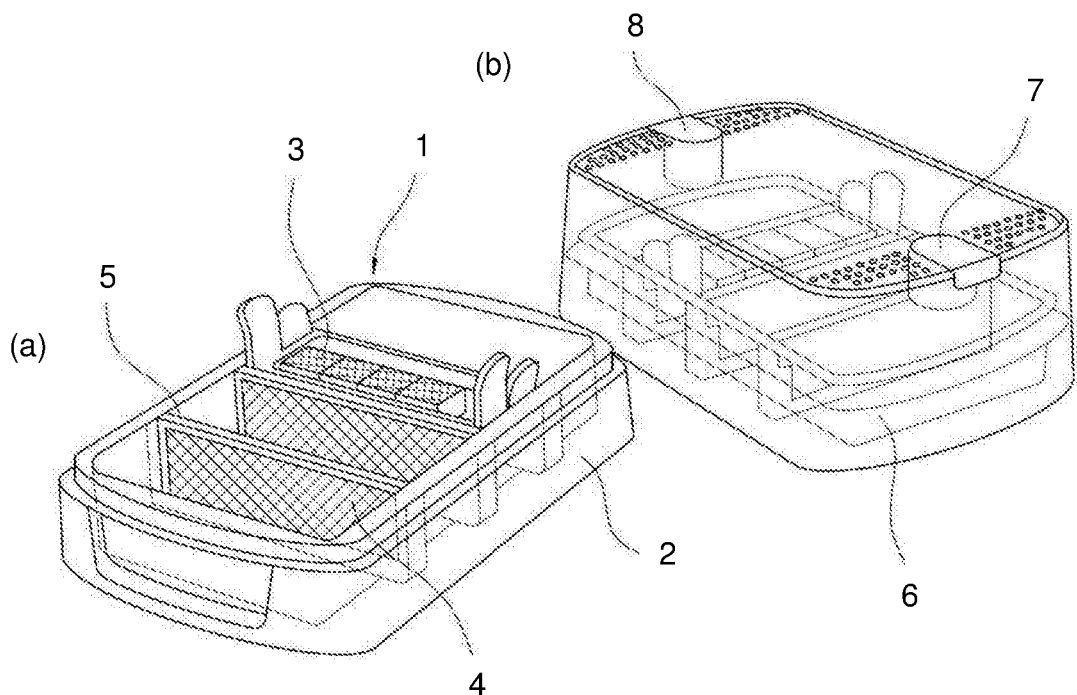

(51) Int. Cl.
    *C12M 1/32*    (2006.01)
    *C12M 3/06*    (2006.01)
(52) U.S. Cl.
    CPC .............. *C12M 25/14* (2013.01); *C12M 3/06* (2013.01); *C12M 23/38* (2013.01)

(56) References Cited

U.S. PATENT DOCUMENTS

| | | | | |
|---|---|---|---|---|
| 2003/0215940 | A1* | 11/2003 | Lacey | C12M 21/06 156/245 |
| 2004/0214313 | A1 | 10/2004 | Zhang et al. | |
| 2007/0082390 | A1* | 4/2007 | Hastings | B01L 3/5085 435/297.5 |
| 2008/0261298 | A1 | 10/2008 | Yonekawa | |
| 2009/0215104 | A1* | 8/2009 | Taboas | C12M 35/02 435/29 |
| 2012/0183987 | A1* | 7/2012 | Gevaert | C12N 5/0693 435/29 |
| 2014/0212964 | A1* | 7/2014 | Cuiffi | C12M 29/00 435/325 |
| 2014/0283356 | A1 | 9/2014 | Nakayama | |
| 2016/0152945 | A1 | 6/2016 | Blahut | |

FOREIGN PATENT DOCUMENTS

| | | |
|---|---|---|
| WO | 2010/048441 A2 | 4/2010 |
| WO | 2011/161480 A1 | 12/2011 |

OTHER PUBLICATIONS

Search Report for Application No. GB1602146.1 (mailed Oct. 31, 2016).

International Preliminary Report on Patentability for International Application No. PCT/GB2017/050286 (mailed Aug. 7, 2018).

* cited by examiner

CELL CULTURE DEVICE

This application is a national stage application under 35 U.S.C. § 371 of PCT Application No. PCT/GB2017/050286, filed Feb. 6, 2017, which claims priority of Great Britain Application No. 1602146.1, filed Feb. 5, 2016, each of which is hereby incorporated by reference in its entirety.

This invention relates to a cell culture device, particularly a modular cell culture device and its component parts.

Cell culture involves the introduction of biological cells into an artificially-created environment including a suitable surface to support the growth of cells, solutions containing nutrients for the cells, and appropriate conditions of temperature, humidity and gaseous atmosphere. In such a system, a researcher is able to measure the cells' response to culture alterations, prospective drugs, the presence or absence of other kinds of cells, carcinogenic agents, and viruses, for example.

A three dimensional cell culture is an artificially-created environment in which biological cells are permitted to grow or interact with its surroundings in all three dimensions. This contrasts with the more conventional two dimensional cell culture, such as in a Petri dish environment, where cells proliferate along a surface. Three dimensional cell cultures are advantageous because they more closely mimic in vivo systems, and allow greater inter-cell interaction to occur. The effects of this inter-cell interaction may therefore be measured and observed.

There are a number of conventional methods for providing three dimensional cell cultures. However, existing methods suffer from a number of disadvantages, including increased complexity and cost, as well as increased difficulty of taking accurate measurements from the cell culture, relative to two dimensional environments. Indeed, invasive measurement techniques in conventional methods, such as those that utilise dyes, may damage or kill cells. Similar problems are also experienced in two dimensional systems.

There has now been devised a cell culture device and a method of providing a cell culture that overcome or substantially mitigate the aforementioned and/or other disadvantages of the prior art.

According to a first aspect of the invention there is provided a cell culture device comprising a container, at least one divider and a plurality of cell growth blocks located within the container wherein the divider separates the container into multiple compartments and the divider is selectively permeable and wherein the cell growth blocks are each independently removable from the container.

The device of the present invention is advantageous primarily because it allows great flexibility in changing experimental conditions. This provides an optimal environment for growth and testing of specific cell types and allows the user to replicate the living environment much more closely. As the cell growth blocks can be placed on either side of the divider and can be independently removed and studied, the effects of substances on the same cells under differing conditions, for example comparing when a substance is in direct contact with the cell with when a substance is only available to the cell when diffused through the divider, or the effect of a substance on different cell types by implanting different cells in each cell growth block can be easily studied.

The cell growth blocks being independently removable is particularly advantageous if it is desired to study the effect of a substance on a particular cell type at regular intervals. Multiple cell growth blocks implanted with the same cell type can be exposed to the desired test substance and at the desired intervals a cell growth block can be removed and studied without disturbing the remaining cell growth blocks.

Furthermore, multiple cell growth blocks containing different cell types can be integrated together to replicate the whole body structure. This can be used to create whole organ structure (heart, lung, skin, liver, etc) all in one device. A range of cells can be grown including primary and immortalised mammalian cell lines, skin, brain, muscle, cardiac, or bone cells as well as bacteria, viruses, fungi etc. By integrated together is meant that the cell growth blocks are in contact and fluid communication with one another. The cell growth blocks may be selectively permeable to allow movement only of particular substances between cell growth blocks.

As the cell growth blocks are independently removable, material (from sub-cellular to single cell to multiple cells) can be biopsied single or multiple times without disrupting the overall experiment.

The cell growth blocks are generally modular three dimensional components that are suitable environments for cell culture.

The cell growth blocks may be any suitable three-dimensional shape, for example a cube, generally cuboid, or spherical. Preferably the cell growth blocks are cuboid. This enables the cell growth blocks to be stacked together more efficiently and to have a greater contact area between blocks if required.

Cell growth blocks may be customised for specific cell types from fibroblasts to epithelial cells and all other cell types such as bacteria and other microorganisms such as fungi, including adherent and suspended cells. These may be primary or immortalised cell lines, of human origin or derived from any other species type.

In use, the cell growth blocks are implanted with the desired cells to be studied and the container is generally filled with a suitable cell growth medium. Substances to be studied can be added to the cell growth medium either generally or to the cell growth medium only on one side of the divider. The container is usually filled with the cell growth medium to a height below that of the divider such that the only means of transport of a substance from one side of the divider to the other is through the divider.

Preferably the cell growth blocks provide a three dimensional cell growth environment. Three dimensional cell growth environments better replicate the living conditions of cells when compared to growing cells in two dimensions where the cells are generally flat and lack the ability to mimic natural environments. If the cells are grown in three dimensions, scaffolds are provided to support the three dimensional cell cultures.

The cell growth block may consist of scaffold or may comprise scaffold and a housing containing the scaffold. The housing may support the scaffold and provide the cell blocks with structural integrity. The housing may also be selectively permeable to allow the movement of cells, cell signalling molecules, nutrients or test substances between the cell growth block and the surrounding environment. The housing may be constructed of any suitable selectively permeable material.

The cell growth blocks may have further application independently of the device according to the first aspect of the invention. Hence according to a further aspect of the invention there is provided a cell growth block for cell culture comprising a three-dimensional scaffold block located within a selectively permeable housing.

Scaffold

The scaffold may be composed of natural or synthetic polymer, or hybrids of natural and synthetic polymers to create three-dimensional in vitro microenvironments to mimic the extracellular matrix (ECM) of native cells and tissues.

The scaffold material may be any suitable material, for example polymers (including hydrogels), tissue constructs, metals, glasses or ceramics. The scaffolds may be formed of synthetic or natural substances. The scaffolds, either individually or in combination, are incorporated into cell growth blocks to mimic the extracellular matrix (ECM) of natural living cells in laboratory conditions.

Preferably the scaffold is a polymer scaffold. Most preferably the scaffold is a hydrogel scaffold.

By hydrogel is meant a polymeric gel in which the liquid component is water.

The scaffolds may comprise one or more natural polymers, for example proteins (such as collagen, fibrin, alginate, gelatine, silk and/or genetically engineered proteins), polysaccharides (such as agarose, carboxymethylcellulose, hyaluronic acid and/or chitosan), DNA, live cells and tissue constructs or any combination of the above.

The scaffolds may comprise one or more biodegradable polymers including polyester containing macromers such as poly($\varepsilon$-caprolactone) (PCL), poly glycolic acid (PGA), and poly lactic acid (PLA).

The scaffolds may comprise non-biodegradable polymers, for example polymers of acrylamide (AAm), monoacrylate (mPEGMA or PEGMA), acrylic acid (AAC) and methoxyl poly(ethylene glycol) (PEG) monoacrylate) (mPEGMA), hydroxyethyl methacrylate (HEMA), 2-hydroxypropyl methacrylate (HPMA), acrylic acid (AAc) and N-isopropylacrylamide (NIPAm), or polystyrene (PS).

The physiochemistry of the scaffold is selected to be suitable for cell growth.

The mechanical strength of the scaffold can be controlled to maintain the properties of the scaffold such as its strength, longevity, stiffness, roughness, viscoelasticity and/or porosity.

The scaffold stiffness may be modified to replicate differing in vivo cell locations.

Different stiffness or roughness is required to culture different cell types (for example a soft scaffold may be required for lung cells, but a hard scaffold may be required for bone cells). Techniques to make hydrogels with specific shear moduli (measured in kPa) and/or specific pore sizes are known (and published). For example, polyacrylamide stiffness is controlled by the relative concentration of acrylamide monomer and its cross-linker. Different types of tissue have different relative stiffness, and the scaffold blocks may be engineered to have a stiffness to match.

Liver, mammary, brain, bone marrow and lung cells generally have a stiffness in the range 100 Pa to 2 kPa. A suitable polyacrylamide hydrogel may be produced using 3% acrylamide (v/v) and 0.06% bis-acrylamide (v/v), to give a hydrogel with Young's shear modulus of around 500 Pa.

Skin, spleen and kidney cells generally have a stiffness in the range 3 kPa to 8 kPa. A suitable polyacrylamide hydrogel may be produced using 5% acrylamide (v/v) and 0.15% bis-acrylamide (v/v), to give a hydrogel with Young's shear modulus of around 5 kPa.

Cardiac, myoblast, arterial, muscle and skeletal cells generally have a stiffness in the range 10 kPa to 20 kPa. A suitable polyacrylamide hydrogel may be produced using 10% acrylamide (v/v) and 0.1% bis-acrylamide (v/v), to give a hydrogel with Young's shear modulus of around 10 kPa.

Pre-calcified bone cells generally have a stiffness in the range 25 kPa to 40 kPa. A suitable polyacrylamide hydrogel may be produced using 10% acrylamide (v/v) and 0.3% bis-acrylamide (v/v), to give a hydrogel with Young's shear modulus of around 35 kPa.

It will be clear to those skilled in the art that hydrogels of other stiffness may be produced by suitably varying the ingredients.

The mechanical properties of the scaffold may be selected to allow shape formation or maintenance of the cells during cell growth.

The mechanical properties of a scaffold may be controlled by using a combination of materials. For example, the properties of a hydrogel scaffold may be controlled by using an inorganic or organic material in combination with the hydrogel, for example ceramics, metals, other hydrogels or any other suitable structure.

The scaffold may be porous or non-porous. If the scaffold is porous, the pore distribution, pore structure and pore size can be controlled.

If the scaffold is porous, the pores may have a specific pore size (nm, µm or mm) to allow the movement of cells, cell signalling molecules, nutrients or test substances either through the matrix, surface or at specified locations or to remove waste substances.

Thus the scaffold may be selectively permeable to control the diffusion of specific test substances, cell signalling molecules, nutrients and other test agents, for example nanoparticles, viruses, or bacteria, through the scaffold and/or cell growth block, or from one block to another.

The porosity of the scaffold can be modified such that the diffusion of certain substances and their rate of diffusion can be selected. This could influence cell division, cell growth, cell death and other phenotypic changes designated as physiological, pharmacological or toxicological.

The scaffold material may allow the controlled diffusion, through its modified porosity, of agents (pharmaceuticals, toxins, agents, physical entities including nanoparticles, cell factors) towards a cell population growing on the outer surface of the scaffold. This replicates more faithfully exposure settings that occur in vivo within an in vitro setting—situations this could replicate include the diffusion of inhaled entities through lung cells into the systemic circulation, diffusion across the blood brain barrier, diffusion across the GI tract, diffusion across blood vessels such as capillaries into surrounding cells, and diffusion across all barriers (physiological and non-physiological) to influence adjacent cell populations.

The scaffold may permit diffusion of substances such as nutrients or drugs.

The scaffold may be manufactured with a pore size that provides a desired diffusion rate for a particular substance, or particular substances. Alternatively, the scaffold may be manufactured such that diffusion rates for the relevant substance(s) are known. For many diffusive materials, reference tables of a wide range of cation diffusion rates and anion diffusion rates are available. Alternatively, diffusion rates may be determined using known diffusion rate test equipment.

The scaffold may have varied pore sizes selected to enhance the growth of different specific cell types. For example, for fibroblasts and epithelial cells, pore size might range from 5 µm to 100 µm, for endothelial cells about 25 µm, and for vascular smooth muscle cells, 63-100 µm. For tissue regeneration a minimum pore size of 100 µm can simulate mitigation conditions but the pore size is preferably 300 μm to improve bone formation and develop a network of capillaries.

Degradation of the scaffold can be controlled for particular cell growth, for example for implants used in tissue regeneration.

The surface area of the scaffold may be modified and/or activated by incorporation of active functional groups (for example peptides) to increase support for cell growth and for mitigating scaffold degradation. The polarity of the scaffold may be modified to increase cell adhesion and the spreading of living cells, for example by adding proteins, changing the charge of the surface groups, or by the addition of peptides. Cell adhesion may be increased by inserting structural motifs within the scaffold. For example, a negative surface charge can increase cell attachment.

The scaffold may be supported by other materials to give a specific shape (eg square) or to maintain its structure. The supporting material for the scaffold block may be any suitable material, for example, plastic, metal, ceramic or glass.

Antibodies, scaffolds or other structures (including nanostructures) could be adsorbed onto the surface of these supporting materials to selectively adhere or manipulate specific cell types for selective clonal expansion or isolation from a particular cell population.

Other proteins such as plasma proteins (e.g., albumin) may be contained within a scaffold; these are commonly found in blood and influence the kinetics (absorption, metabolism and excretion) of pharmaceuticals and toxic agents.

The scaffold may be formed with an outer layer which may be advantageously modified to improve cell attachment and better support cell growth and differentiation. Such a layer may comprise hydrogel. In particular, a layer of hydrogel may include an outer surface coated with an Extra-Cellular Matrix ("ECM").

A hydrogel outer layer of the scaffold may be formed to match one or more properties of the cells and/or tissue desired to grow there. Such properties may include rigidity, stiffness and/or other native properties of different body tissues.

The outer layer may constitute the housing for the cell growth block as discussed above.

A combination of scaffold materials may be provided to create a matrix suitable for cell growth. A plurality of different surfaces may be provided in different regions of the device to encourage growth of different types of cell.

The surface of the scaffold may be provided with microscopic roughness and/or macroscopic structure to provide favourable growth environments for specific types of cell.

The scaffold material may allow the controlled diffusion, through its modified porosity, of agents (pharmaceuticals, toxins, agents, physical entities including nanoparticles, cell factors) towards a cell population growing on the outer surface of the scaffold. This replicates more faithfully exposure settings that occur in vivo within an in vitro setting—situations this could replicate include the diffusion of inhaled entities through lung cells into the systemic circulation, diffusion across the blood brain barrier, diffusion across the GI tract, diffusion across blood vessels such as capillaries into surrounding cells, and diffusion across all barriers (physiological and non-physiological) to influence adjacent cell populations in other cell growth blocks.

The device may be compartmentalised with scaffold blocks to allow for co-culture of differing cells types with or without the different cell types coming into contact, eg fibroblasts and epithelial cells, differing epithelial cells, bacteria/virus particles and mammalian cells. Designated filtration pores may allow transfer of factors from one cell type to another. This enables the study of the effects of one cell on another. Co-culture systems are composed of at least two different cell types in order to simulate cell-cell interaction of the in vivo microenvironment of natural tissue, for example in cancer studies. Experimental conditions that the device may replicate include breast cancer models, by co-culturing breast carcinoma or parenchymal cells with stromal cells (i.e., fibroblasts adipocytes, lymphocytes and epithelial cells), human skin models by co-culturing dermal fibroblasts with keratinocytes, and healthy or damaged neurones, by co-culturing peripheral and central nervous systems in combination of glia cells (eg, astrocytes) together with oligodendrocytes.

Different eukaryotic cells (eg fibroblasts, epithelial cells), prokaryotic cells with eukaryotic cells, viral particles with eukaryotic cells or viral particles with prokaryotic cells may be studied. The scaffold prevents actual cell-to-cell contact but permits the diffusion of factors from one cell type to another in order to ascertain their effect on the other cell type. The true effects of stromal factors or infectious secretions in isolation of cell-to-cell contact can be examined.

Scaffold blocks may be provided with or without cells, and may require modification prior to use.

Dividers

The at least one divider separates the container into multiple compartments. The at least one divider is selectively permeable to allow the transfer of specific substances, such as cell signalling molecules, nutrients or test substances, but prevent others. The dividers will generally prevent the transport of cells across of the divider.

The dividers may comprise an engagement means for engagement with a corresponding engagement means on the container or other dividers, in order to retain each divider in the desired position and ensure a proper seal between each compartment, such that material may only transfer between compartments through the selectively permeable divider.

Both the horizontal and vertical dividers may be removable and interchangeable to vary experimental conditions prior or during experimentations.

Non-porous barriers may also be used within the device to isolate specific cell populations and media from other compartments.

The dividers may engage with the container or other dividers in a vertical orientation or a horizontal orientation. Dividers that are oriented horizontally may be located between layers of cell growth blocks in a stack of cell growth blocks. The horizontal dividers may be provided with formations that facilitate their removal from the container along with the cell growth blocks stacked upon them. A combination of vertically and horizontally oriented dividers may be utilised in order to separate the container into chambers.

For example one compartment may contain cell growth blocks and another compartment may contain media incorporating a test substance (for instance, drugs, chemical pollutants, viruses, bacteria) and the diffusion of the test substance can then be controlled to replicate living conditions. A divider will serve as a diffusive layer to control the movement or selection of material allowed to cross the barrier. For example, cancerous cell culture can be exposed to the testing substance at a diffusion rate that is controlled to replicate the environment of living tissue.

Multiple dividers may be used to separate the container into a desired number of compartments.

The cell growth blocks may all be located on one side of the divider, ie in one compartment, or some may be located on one side of the divider and some on the other. This enables the user to have control over which cell growth blocks are exposed to which test substances.

The dividers may be made of the same material as the scaffolds mentioned above and include natural and/or artificial polymers (including hydrogels), tissue constructs, metals, glasses and ceramics. The divider may comprise one or more natural polymers, for example proteins (such as collagen, fibrin, alginate, gelatine, silk and/or genetically engineered proteins), polysaccharides (such as agarose, carboxymethylcellulose, hyaluronic acid and/or chitosan, live cells and tissue constructs or any combination of the above.

Porous hydrogel used for selective diffusion may be classified for example as an open pore hydrogel or restricted hydrogel. For example, a hydrogel may be formed from polyacrylamide cross-linked with a derivative of agarose (a polysaccharide polymer), to form a hydrogel known as an open pore diffusive gel. The hydrogel may be an agarose gel or collagen matrix. The hydrogel may be a bis-cross-linked acrylamide gel (known as restricted gel). For agarose, open pore and restricted hydrogels, reference tables of a wide range of cation and anion diffusion rates are known (and published).

Dividers may also replicate the skin with commercially available cell culture and products, for example keratinocyte, fibroblast or basal membrane proteins or skin grafts.

The dividers may comprise a supporting frame to support the filter materials. The supporting frame may include walls or a mesh structure. The supporting frame may be made of the same materials as the filters in the dividers but may also include harder materials to aid handling of the dividers and their incorporation in the tray.

These harder materials may include: polystyrene (PS), acrylic copolymer (AV), polyvinyl chloride (PVC), polypropolyne (PP), glass (borosilicate), ceramics, metallic materials (eg, stainless steel)

Simulated skin barriers may also be created using artificially composed polymers. The blood brain barrier may be simulated by using a co-culture of cells types such as epithelial cells, astrocytes, or pericytes.

The filters incorporated in the dividers may be hydrophilic or hydrophobic in nature and composed of a range of organic and/or inorganic materials including metals, polymers (natural and synthetic), glass or ceramic. The dividers may be constructed to allow nanofiltration, microfiltration or ultrafiltration of substances between cell growth blocks with pore size ranging from 1-100 nm, 1-100 µm or larger, for example 1-20 nm, 20-40 nm, 40-60 nm, 60-80 nm, 80-100 nm, 1-20 µm, 20-40 µm, 40-60 µm, 60-80 µm or 80-100 µm. Filters in dividers might be composed of hydrophilic or hydrophobic properties depending on the experiment to be conducted. The dividers may be used for protein extraction, purification of virus filtration, buffer exchange, sterilisation, blood plasma fractioning, DNA extraction or collection of biological material (DNA, protein etc) released by cells which is achieved by using filters with different pore size. For example, a large pore ultrafiltration could be constructed to filter molecules of sizes ranging from 100-500 kDa. For instance, virus filters and low protein binding filters might be composed of polyvinylidene fluoride (PVDF), polyether sulfone (PES), or cuprammonium regenerated cellulose filters with pore size ratings of 15 nm-75 nm.

Filters may be made from the following materials, either on their own or in combination, including cellulose based filters (e.g. cellulose acetate, cellulose nitrate, mixed cellulose esters), polyether sulfone (PES), PTFE (polytetrafluoroethylene), silica gel membrane, Nylon, polyester, polycarbonate, stainless steel and ceramic membranes.

The filters may be single layer or alternatively multilayer by combining layers of any of the above materials.

The delivery of test agents can therefore be controlled to replicate in vivo conditions and lead towards toxicity testing.

By modifying the thickness, pore size, or composition different in vivo barriers can be simulated, for example the blood brain barrier vs. kidney glomerulus.

The dividers may be transparent, semi-transparent or non-transparent.

Container

The container may be any suitable size and shape for retaining the cell growth blocks. The size of the container will vary based on the type of experiment to be performed. For maintained cell culture the size may range from 25 mm to 250 mm or more. Commonly the container is tray shaped ie the container is shallow in depth.

A larger size of container could be used for tissue regeneration.

The container may comprise an engagement means for engaging with corresponding engagement means on the dividers and cell growth blocks in order to retain each divider and cell growth block in the desired position and, in the case of the dividers, ensure a proper seal between each compartment, such that material may only transfer between compartments through the selectively permeable divider. The engagement means may comprise corresponding recesses and projections in the container, dividers and cell growth blocks. The container may comprise allocated engagement means for cell growth blocks and dividers for varied experiments. The number of cell growth blocks and allocated slots may range from 1-384, or more.

The container may be provided with recesses, such as grooves, and the cell growth blocks with corresponding projections which fit in the grooves when the cell growth blocks are located in the container and limit movement of the blocks within the container. Alternatively the container may be provided with projections and the cell growth blocks with corresponding recesses.

The container may be constructed to the size of standard multiwall plates to comply with other analysis techniques. Standard multiwall plates for cell culture are constructed with standard dimensions of L127.8×W85.5×H14.4 mm and a standard number of well plates eg 6, 12, 24, 48, 96, 192, 384 etc.

The dividers may be constructed to cover the whole length, width and the height of the container. For example 85.5 mm×14.4 mm, or 127.8 mm×14.4 mm.

Dividers may also be placed on the top of one or more cell growth blocks.

For example for a block with a depth×length×height (10 mm×10 mm×10 mm) a divider of 10 mm×10 mm may be constructed to be placed adjacent or on top of a scaffold block as required.

A divider may be placed across the width of the container (eg. 85.5 mm×14.4 mm) to divide a media compartment from the growing cells in order to control the exchange of substances across the divider.

Dividers may be placed in the container at designated areas using aseptic techniques such as sterilised tweezers or a kit may be provided. Allocated slots for varying dividers may be constructed and a divider would fit into the slots available on the container or on the pre-constructed cell growth blocks. When a divider is placed on top of the cell growth block the block will also contain slots for further dividers.

The container may be transparent, semi-transparent or non-transparent. The container may be designed to allow or stop specific electromagnetic radiation eg, UV for specific experiments.

The container may be provided with a lid. The lid may be constructed from the same materials as the container. For example it may be moulded from polycarbonate, polyethylene, or polystyrene. The lid may fit closely on the top of the tray but also permit air flow. The lid may be constructed with a loose fit to allow gas exchange or alternatively, air filters may be incorporated in the chamber to allow the gas exchange to be filtered (eg, 0.2 µm pore size) but prevent microbes to pass through—this reduces the chance of contamination of the sample(s). Examples of air filters that may be incorporated in the device include hydrophobic PTFE (Teflon) filters.

The container may incorporate a specialised window made of a different material. This is advantageous as it enables the user to do different experiments to the same cells.

If the container is provided with a window, a microscope may be used to study the cells, for example the window may be Raman suitable to enable Raman spectroscopy measurements to be taken, or the window may be a standard transparent window for use with a conventional microscope or probe.

The container is advantageously sized such that it fits under a microscope.

The container may further comprise integrated visualizing devices, for example a camera that streams and records changes happening in the device in real time.

Sensors can be incorporated in the cell growth blocks, dividers or container to measure inflow or outflow of media and gas content.

The sensors may be removable.

The sensors may be analytical, spectrochemical, electrical, elemental, or optical sensors including nanosensors (for instance, based on graphene, C60 fullerene, or other nanoparticles). The sensors can be used to sense electrical/chemical impulses or movements of differing cell types, track the development of either single cells or populations of cells, determine cell-to-cell interactions, respiration of cells, varying hardness and thickness of individual cells or cell colonies, determine cell lineage (the hierarchy of cells within a given cell population from stem cell to differentiated cell) and cell-to-cell signalling (eg via chemical factors, enzymes, reductive or oxidative processes, exosomes, proteins, liposomes, RNA or DNA molecules, viral or nanoparticles)

In use, cells can be implanted within the scaffold at varying depths in order to modify oxygen tension, ie the partial pressure of oxygen present. This is to replicate the varying oxygen tension one might find in a human tissue or disease state. For instance, as one enters the crypt of the GI tract the cells hidden at the base of the crypt are likely protected from the damaging effects of high oxygen tension and are likely to contain stem cells. In cancer, as a tumour grows there are hypoxic regions—these may contain cancer stem cells and are less amenable to treatment. This device allows one to replicate these scenarios.

Colonies of cells can be implanted into the scaffold.

The device may be used to produce surgical implants. The device may be pre-incubated in order to populate the implantable material with specific cell types (eg osteocytes) prior to surgical implantation. This implantable material could be populated with stem cells in order to allow cell adhesion of donor cells for autotransplant, allotransplant or xenotransplant.

Spaces could also be created in the device for input of removable implant material. This would allow transfer-culture of cells on the scaffold to the implant prior to use of an implant in surgery. This could allow for growth of bone, cartilage or arteries for example.

The device may also be used as an in vitro variable simulation of the in vivo basement membrane. For instance, one scaffold's stiffness can replicate the prostate epithelial cell basement membrane whilst another can replicate that in breast tissue. A basement membrane is a modifiable substrate upon which differing cell types can grow and differentiate. The roughness of the scaffold may determine the ability of specific cell types to adhere to the scaffold.

As described above the cell culture device is of use in a method of cell culture. Thus according to a further embodiment of the invention there is provided a method for culturing cells comprising the steps of (a) inserting a plurality of cell growth blocks and one or more dividers into a container, (b) implanting one or more types of cells in the cell growth blocks, and (c) adding a cell growth medium to the container. Steps (a) and (b) may be performed in any order.

It will be appreciated that the cell growth blocks, dividers and container of the method may have any of the features discussed above in relation to the device according to the first aspect of the invention.

The components of the cell culture device of the invention may be provided as a kit. Thus in a further embodiment of the invention there is provided a kit for a cell culture device comprising a plurality of cell growth blocks, a container suitable for housing said cell growth blocks, and a selectively permeable divider suitable for separating the container into multiple compartments.

It will be appreciated that the components of the kit may have any of the features discussed above in relation to the device according to the first aspect of the invention.

Figure 2:
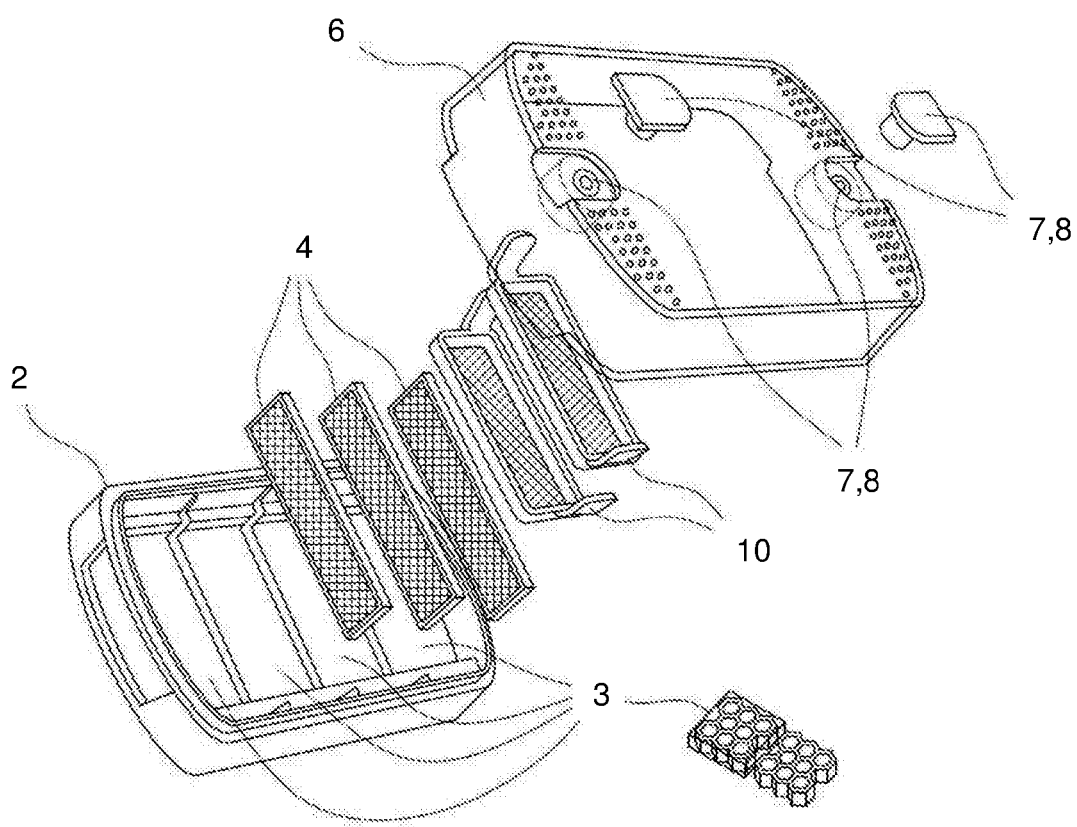
Figure 3:
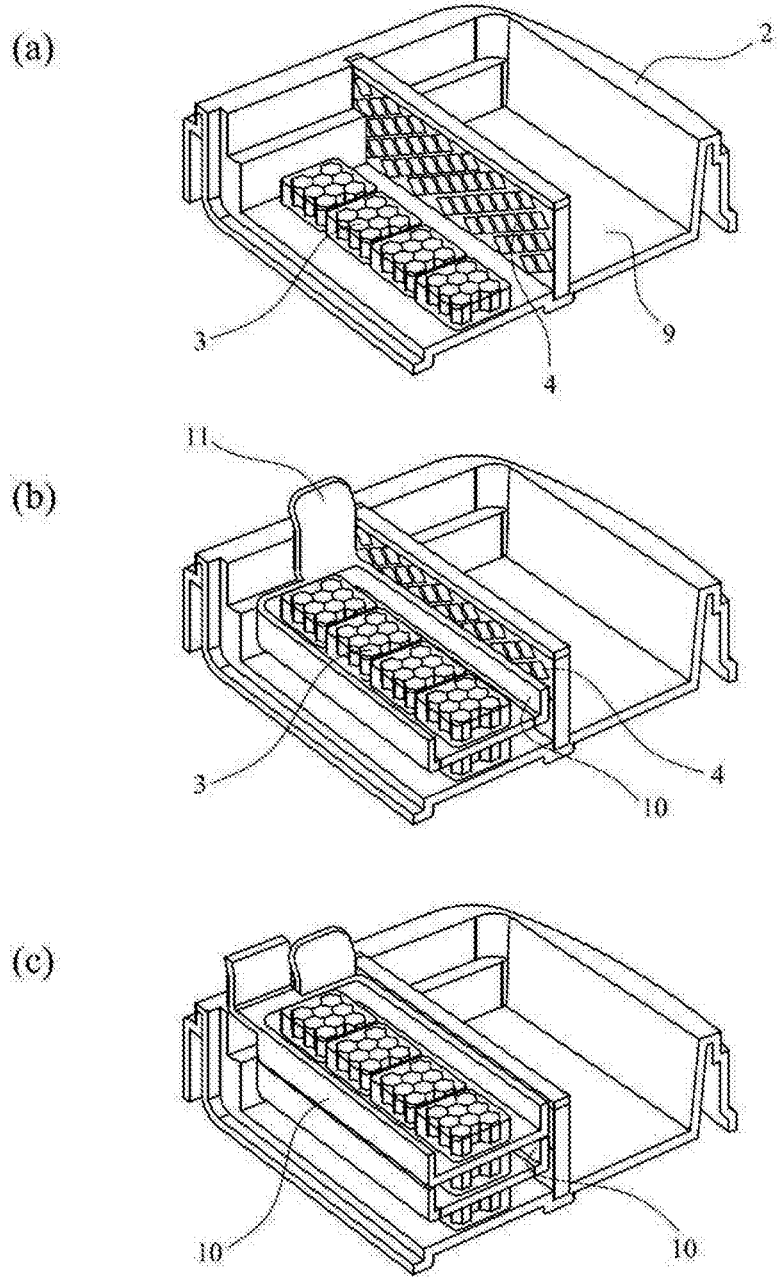
Figure 4:
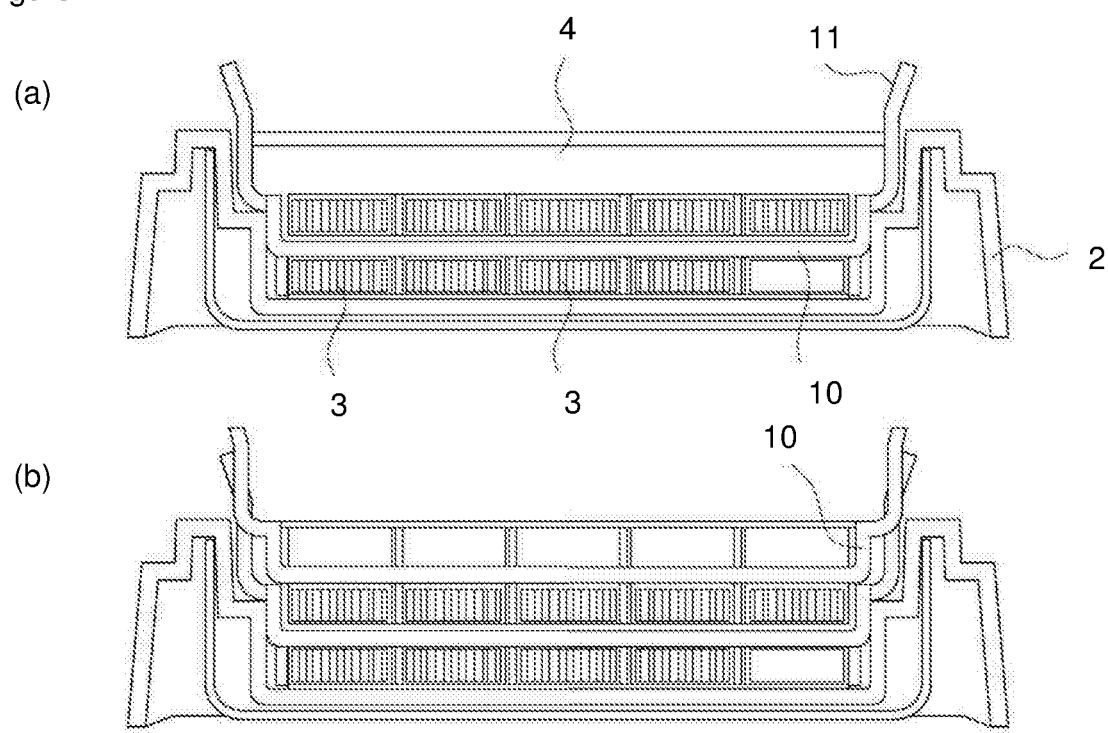

An embodiment of the invention will now be described in greater detail, by way of illustration only, with reference to the accompanying drawings, in which FIG. 1 shows a perspective view of an embodiment of a device according to the invention both (a) without and (b) with its lid FIG. 2 shows the device of FIG. 1 as an exploded perspective view FIG. 3 shows a perspective view of an alternative embodiment of a device according to the invention where the device is set up for a particular experiment FIG. 4 shows a perspective view of a further alternative embodiment of a device according to the invention where the device is set up for an alternative experiment Referring first to FIG. 1, a first embodiment of a cell culture device (1) is shown. The device (1) generally comprises a rectangular outer tray (2), five cell growth blocks (3) and three diffusive dividers (4).

The tray (2) is transparent and moulded from polycarbonate. The tray (2) is shallow and is provided with narrow troughs across its base which extend between one pair of parallel walls of the tray and perpendicular to the opposing pair of parallel walls. The troughs are spaced at intervals across the base of the tray that correspond to the width of the cell growth blocks and are shaped such that they can receive corresponding protrusions present on the bases of the cell growth blocks (3) or the dividers (4).

The cell growth blocks (3) are rectangular in cross section and comprise selectively permeable walls and a solid base. The walls and base are moulded from polycarbonate. The walls are sufficiently porous to allow transport of growth media into the cell growth block and metabolites to pass out of the block (3) but at the same time retain the cells within the block (3). The base is provided with protrusions which extend down from the base. In use these protrusions engage with the corresponding troughs in the tray (2) and restrain the movement of the blocks (3) within the tray (2). Each cell growth block (3) contains a porous scaffold material. The scaffolds comprise a hydrogel as described below. The scaffold acts as a three-dimensional structure on which implanted cells can grow. The scaffold is coated with biocompatible material to support 3D cell culture growth.

The cell growth blocks (3) are positioned in the tray (2) such that the sides of the blocks (3) are touching one another. If different types of cells are grown in each cell growth block, the close proximity enables transfer of cell growth signals between the different types of cells but the selectively permeable walls prevent the cells from migrating into other blocks.

The tray (2) is divided into multiple compartments by the diffusive dividers (4). The diffusive dividers (4) extend across the width of the tray (2) and up the majority of the height of the walls of the tray (2). The divider (4) has the same porosity as a biological barrier, for example the blood-brain barrier, and therefore allows the same types of molecules to pass through. The dividers (4) comprise a supporting frame (5) which supports the filter material. The supporting frame (5) is moulded from polycarbonate and the filter supported within the frame is a nylon membrane with a 2 μm pore size.

The tray (2) is provided with a lid (6) moulded from polycarbonate. Gas inlets and outlets (7,8) are provided at opposite ends of the lid. The lid (6) is moulded to fit closely on the top of the tray (2). Two 0.2 μm pore size hydrophobic PTFE air filters are incorporated in the lid to allow the gas exchange to be filtered but prevent microbes to pass through—this reduces the chance of contamination of the sample(s).

In use, the scaffolds are seeded with the cells desired to be grown and the tray (2) is filled with a growth medium to a height below that of the diffusive divider (4).

Further possible arrangements of the device according to the invention are shown in FIGS. 3 and 4.

In FIG. 3 the outer tray (2) is divided into two compartments by a diffusive divider (4). In the device of FIGS. 3a to c, multiple cell growth blocks (3) are located on one side of the diffusive divider (4). The other side of the divider (4) acts as a reservoir (9) to which substances of interest may be added. In FIGS. 3b and 3c the cell growth blocks (3) are stacked on top of other cell growth blocks. Horizontal permeable dividers (10) are placed between each layer of cell growth blocks (3). Each horizontal divider (10) is provided with a tab (11) that facilitates the removal of the divider (10), and any cell growth blocks (3) stacked on it, from the tray (2). This formation permits the user to allow controlled movement of substances both horizontally and vertically.

In use, as for the device of FIG. 1, the scaffolds are seeded with the cells desired to be grown and the tray (2) is filled with a growth medium to a height below that of the diffusive divider (4). The tray (2) is provided with a lid moulded from polycarbonate that fits closely on the top of the tray (2).

The arrangement of FIG. 3a allows cells to be grown that can have growth conditions which are identical apart from one variant, ie direct access to a particular compound of interest versus access only through a particular divider. Stacking the blocks (3) also allows closer mimicry of the three dimensional aspects of cell growth within a natural environment for example cells derived from different organs of the body may be in close proximity to multiple other different cell types.

In FIG. 4, the tray (2) is divided into multiple horizontal and vertical compartments by means of multiple scaffold blocks (3) further separated by one, in the case of FIG. 4a, and two, in the case of FIG. 4b, horizontal dividers (10).

A method of preparing a hydrogel suitable for being moulded into a cubical form (for embodiments of the present invention) is set out below. This method comprises three principal steps of (i) preparation of a hydrogel scaffold block; (ii) activation of the surface of the hydrogel to allow attachment of an ECM; and (iii) coating of the activated surface of the hydrogel with an appropriate concentration of ECM.

Chemicals

40% Acrylamide Solution (Bio-Rad cat number 161-0140)
Cross-linker (2% bis-acrylamide, Bio-Rad catalogue number 161-0143)
1M HEPES buffer (N-2-Hydroxyethylpiperazine-N-2-Ethane Sulfonic Acid buffer, eg Sigma-Aldrich catalogue number 83264)
Phosphate-buffered saline (PBS) sterile (eg Life Technologies catalogue number 20012027)
Ammonium persulphate ("APS" eg Sigma-Aldrich catalogue number A3678)—10% required, 0.1 g in 1 g in $ddH_2O$
N,N,N'N'-Tetramethylethylenediamine ("TEMED" Sigma-Aldrich catalogue number T9281)
Sulfo-SANPAH (Thermo Scientific catalogue number 22589)
Dimethylsulfoxide ("DMSO" Sigma-Aldrich catalogue number D2438)
Extracellular Matrix ("ECM") protein (eg collagen, fibronectin or synthetic peptides) eg Collagen type 1 (Life Technologies catalogue number A1048301)
deuterium depleted (dd) $H_2O$
Ethanol Materials/Facilities 0.45 μm filter (eg Merck Millipore catalogue number SLHV033RS)
Sterile forceps
20 mL sterile syringe
Cube formers (eg with inner dimensions of 10 mm×10 mm×10 mm). It will be clear to those skilled in the art that cube formers of different sizes and/or shapes may be used to produce by moulding, components with a range of different surface structure.
Laminar flow hood Step 1: Preparation of Hydrogel (eg Polyacrylamide)

1.1. Acid wash cube formers, scaffold block support structures. Rinse with $ddH_2O$ and then air dry on rack in laminar hood. Further sterilise by spraying with 70% ethanol and air dry on a rack in laminar hood.

1.2. Prepare solution of polyacrylamide for desired modulus and/or pore size in the hood by mixing together relative concentrations of acrylamide, cross-linker and ddH$_2$O.

To make polyacrylamide gel with shear modulus of about 9 kPa, a total of 10 mL is sufficient to make ten hydrogel scaffold blocks of 10 mm×10 mm×10 mm In a sterile conical mix together:
1.25 mL of 40% acrylamide stock solution
1.5 mL of 2% bis-acrylamide stock solution
7.25 mL of ddH$_2$O Make sure that the gel solution is well mixed by gently shaking and stirring.

NB: Gel solution can be stored in a refrigerator (4° C.) for at least three months.

1.3. Add 1/100 aliquot of 10% APS; eg 100 µl of 10% APS for 10 mL solution.

1.4. Add 1/1,000 aliquot of TEMED; eg 10 µl of TEMED for 10 mL solution.

1.5. Quickly run the solution through the 0.45 µm filter to sterilise.

1.6. Pipette the solution into cube formers. If air bubbles appear, tilt and/or agitate to remove bubbles before continuing to pipette. Appropriately shaped cube formers should be used to give the desired shape of the device 1.7. Maintain the assembly in the hood at room temperature for at least 1 hour until the gel is completely set (no liquid remains).

1.8. After the gel has set, remove from cube formers and place the gel in a sterile Petri dish.

NB: Formed gels can be stored at 4° C. for long period of time by keeping them hydrated in buffer (eg PBS) or water.

Step 2: Activation of Polyacrylamide Surface

Prepare 25 mg/mL of sulfo-SANAPAH stock solutions from 50 mg powder using DMSO.

NB: Stock solutions can be stored at −80° C. for 1 year.

2.1. Thaw 120 µL of sulfo-SANAPAH stock solution and add 2,880 µL of ddH$_2$O.

NB: 3 mL is sufficient to coat 10 hydrogel scaffold blocks.

2.2. Add 0.2 mL of sulfo-SANAPAH to all outer surface of each gel and make sure that the entire surface is covered. If not all areas are covered repeat this action until the coating appears uniform.

2.3. Place gel under 365 UV light at a distance of approximately 10 cm and expose for 10 min to activate. Photo-activation darkens sulfo-SANPAH treated surface.

2.4. Rinse each gel with 3 mL of PBS at least 3 times to remove excess sulfo-SANPAH Where multiple layers are required, the above process is repeated, building up additional layers on the existing layers. Preferably the inner layers are created before the outer layers.

Step 3: ECM Crosslinking to Polyacrylamide 3.1. Add preferred ECM protein on the outer surface of hydrogel cube (eg 0.1 mg/mL collagen or fibronectin) prepared in PBS or HEPES buffer. Use 0.1 mL of ECM solution per hydrogel cube. Leave for 12 hours at 4° C. to allow all ECM to crosslink to polyacrylamide.

3.2. Rinse gels extensively with sterile PBS. ECM coated gels can be stored in PBS at 4° C. for up to 2 week. To sterilise gels further prior to use, cover gels in a thin layer of PBS and expose to germicidal UV lamp in flow hood for at least 30 min.

3.3. Once the scaffold blocks are formed, cells of interest are prepared using standard well known laboratory techniques and seeded directly on the hydrogel surface or suspended in ECM before addition. Typically 30,000 to 100,000 cells per hydrogel scaffold are added, depending on experiment and cell type, and allowed to adhere. Hydrogels are initially rinsed with warm sterile PBS and media (37.5° C.) before application of cells.

The invention claimed is:

1. A cell culture device comprising:
a container;
a plurality of dividers that separate the container into multiple compartments and which are selectively permeable to allow the transfer of some molecular substances between compartments but prevent the transfer of others, wherein the container and the at least one divider comprise corresponding recesses and protrusions that are engaged with each other in order to retain the dividers in the desired position within the container, each of the dividers being independently removable from the container; and
a plurality of cell growth blocks located within at least two of the multiple compartments, each being independently removable from the container, wherein the at least two compartments are in fluid communication with one another.

2. The cell culture device of claim 1 wherein the device further comprises a cell growth medium.

3. The cell culture device of claim 1 wherein the cell growth blocks are selectively permeable.

4. The cell culture device of claim 1 wherein the cell growth blocks are implanted with a plurality of different cell types.

5. The cell culture device of claim 1 wherein the properties of the cell growth blocks are adapted for the culturing of a particular cell type.

6. The cell culture device of claim 1 wherein the cell growth blocks comprise a scaffold which provides a three dimensional cell growth environment.

7. The cell culture device of claim 6 wherein the cell growth blocks consist only of the scaffold.

8. The cell culture device of claim 6 wherein the cell growth blocks further comprise a housing to support the scaffold.

9. The cell culture device of claim 8 wherein the housing is selectively permeable.

10. The cell culture device of claim 6 wherein the scaffold is a polymer scaffold comprising a natural or synthetic polymer, or a hybrid of natural and synthetic polymers.

11. The cell culture device of claim 10 wherein the polymer scaffold is a hydrogel scaffold.

12. The cell culture device of claim 6 wherein the scaffold is coated with an extra cellular matrix.

13. The cell culture device of claim 6 wherein the scaffold is porous.

14. The cell culture device of claim 13 wherein the pores are sized in the range of 5 µm to 300 µm.

15. The cell culture device of claim 1 wherein the cell growth blocks are stackable.

16. The cell culture device of claim 1 wherein the container comprises one or more engagement means for engagement with a corresponding engagement means on the cell growth blocks, in order to retain each cell growth block in the desired position within the container.

17. The cell culture device of claim 1 wherein the container has dimensions that correspond to those of a conventional multiwell plate.

18. The cell culture device of claim 1 wherein the container further comprises a lid sized to fit on top of the container.

19. The cell culture device of claim 18 wherein the lid comprises one or more air filters.

20. The cell culture device of claim 1 wherein the container further comprises one or more sensors.

21. The cell culture device of claim 20 wherein the sensors are selected from the group consisting of analytical, spectrochemical, electrical, elemental, or optical sensors.

22. The cell culture device of claim 1 wherein the at least one divider comprises pores having a diameter in the range 1-100 nm or 1-100 µm.

23. The cell culture device of claim 1 wherein the divider is adapted to replicate the properties of a biological barrier.

24. The cell culture device of claim 1 wherein the divider comprises a nylon membrane with a 2 µm pore size as a semipermeable material.

25. The cell culture device of claim 1 wherein the divider further comprises a supporting frame.

26. The cell culture device of claim 1 wherein one or more of the dividers is orientated horizontally in use so as to divide the container or part of the container into top and bottom compartments.

27. The cell culture device of claim 1 wherein the container and the cell growth blocks comprise corresponding recesses and protrusions that are engaged with each other in order to retain the cell growth blocks in the desired position within the container.

28. A cell culture device comprising:
a container;
at least one divider that separates the container into multiple compartments and is selectively permeable to allow the transfer of some molecular substances between compartments but prevent the transfer of others, wherein the container and the at least one divider comprise corresponding recesses and protrusions that are engaged with each other in order to retain the at least one divider in the desired position within the container; and
a plurality of cell growth blocks located within the compartments and each independently removable from the container.

29. The cell culture device of claim 28 wherein the device further comprises a cell growth medium.

30. The cell culture device of claim 28 wherein the cell growth blocks are selectively permeable.

31. The cell culture device of claim 28 wherein the cell growth blocks are implanted with a plurality of different cell types.

32. The cell culture device of claim 28 wherein the properties of the cell growth blocks are adapted for the culturing of a particular cell type.

33. The cell culture device of claim 28 wherein the cell growth blocks comprise a scaffold which provides a three dimensional cell growth environment.

34. The cell culture device of claim 33 wherein the cell growth blocks consist only of the scaffold.

35. The cell culture device of claim 33 wherein the cell growth blocks further comprise a housing to support the scaffold.

36. The cell culture device of claim 35 wherein the housing is selectively permeable.

37. The cell culture device of claim 33 wherein the scaffold is a polymer scaffold comprising a natural or synthetic polymer, or a hybrid of natural and synthetic polymers.

38. The cell culture device of claim 37 wherein the polymer scaffold is a hydrogel scaffold.

39. The cell culture device of claim 33 wherein the scaffold is coated with an extra cellular matrix.

40. The cell culture device of claim 33 wherein the scaffold is porous.

41. The cell culture device of claim 40 wherein the pores are sized in the range of 5 µm to 300 µm.

42. The cell culture device of claim 28 wherein the cell growth blocks are stackable.

43. The cell culture device of claim 28 wherein the container comprises one or more engagement means for engagement with a corresponding engagement means on the cell growth blocks, in order to retain each cell growth block in the desired position within the container.

44. The cell culture device of claim 28 wherein the container has dimensions that correspond to those of a conventional multiwell plate.

45. The cell culture device of claim 28 wherein the container further comprises a lid sized to fit on top of the container.

46. The cell culture device of claim 45 wherein the lid comprises one or more air filters.

47. The cell culture device of claim 28 wherein the container further comprises one or more sensors.

48. The cell culture device of claim 47 wherein the sensors are selected from the group consisting of analytical, spectrochemical, electrical, elemental, or optical sensors.

49. The cell culture device of claim 28 wherein the at least one divider comprises pores having a diameter in the range 1-100 nm or 1-100 µm.

50. The cell culture device of claim 28 wherein the divider is adapted to replicate the properties of a biological barrier.

51. The cell culture device of claim 28 wherein the divider comprises a nylon membrane with a 2 µm pore size as a semipermeable material.

52. The cell culture device of claim 28 wherein the divider further comprises a supporting frame.

53. The cell culture device of claim 28 wherein one or more of the dividers is orientated horizontally in use so as to divide the container or part of the container into top and bottom compartments.

54. The cell culture device of claim 28 wherein the cell growth blocks are located in at least two compartments, and the at least two compartments are in fluid communication with one another.

55. The cell culture device of claim 28 which comprises a plurality of dividers, each of the dividers being independently removable from the container.

* * * * *